US011779207B2

(12) United States Patent
Steinmueller

(10) Patent No.: US 11,779,207 B2
(45) Date of Patent: Oct. 10, 2023

(54) METHOD AND VISION TESTING SYSTEM FOR TESTING THE EYES

(71) Applicant: OCULUS OPTIKGERAETE GMBH, Wetzlar (DE)

(72) Inventor: Andreas Steinmueller, Wettenberg (DE)

(73) Assignee: OCULUS OPTIKGERAETE GMBH, Wetzler (DE)

( * ) Notice: Subject to any disclaimer, the term of this patent is extended or adjusted under 35 U.S.C. 154(b) by 550 days.

(21) Appl. No.: 16/746,374

(22) Filed: Jan. 17, 2020

(65) Prior Publication Data

US 2020/0229691 A1 Jul. 23, 2020

(30) Foreign Application Priority Data

Jan. 21, 2019 (DE) ...................... 10 2019 101 409.3

(51) Int. Cl.
*A61B 3/14* (2006.01)
*A61B 3/10* (2006.01)
(Continued)

(52) U.S. Cl.
CPC ............ *A61B 3/103* (2013.01); *A61B 3/0025* (2013.01); *A61B 3/0041* (2013.01);
(Continued)

(58) Field of Classification Search
CPC ..... A61B 3/103; A61B 3/0025; A61B 3/0041; A61B 3/0091; A61B 3/1005; A61B 3/102;
(Continued)

(56) References Cited

U.S. PATENT DOCUMENTS 7,708,406 B2 5/2010 Koest
8,950,866 B2 2/2015 Volkwardt et al.
(Continued)

FOREIGN PATENT DOCUMENTS

DE 102017210577 A1 12/2018
EP 1138257 A1 10/2001
(Continued)

OTHER PUBLICATIONS

European Patent Office, Search Report, Application No. 20151865.1, dated Jun. 18, 2020, 10 pages.

*Primary Examiner* — Mahidere S Sahle
(74) *Attorney, Agent, or Firm* — Quarles & Brady LLP

(57) ABSTRACT

A method for testing the eyes of a test person with the aid of a vision testing system as well as vision testing system, comprising a first measuring device, a second topographic measuring device, a third refractive measuring device and a processing means, an axial length (L) of an eye of the test person being measured with the aid of the first measuring device, a curvature of the cornea of the eye being measured with the aid of the second measuring device, a refractive property of the eye being measured with the aid of the third measuring device, a measurement simultaneously being carried out with the first, second and third measuring device at the eye, measurement data of the measurements of the first, second and third measuring device being processed with the aid of the processing means, said processing means presenting a database with normal data, a comparison of the measurement data with the normal data being carried out and a result of said comparison being issued by means of said processing means.

24 Claims, 1 Drawing Sheet

(51) Int. Cl.
*A61B 3/103* (2006.01)
*A61B 3/00* (2006.01)
*A61B 3/107* (2006.01)
*A61B 3/12* (2006.01)
*A61B 3/18* (2006.01)
*A61B 8/10* (2006.01)
*A61B 5/00* (2006.01)

(52) U.S. Cl.
CPC ............ *A61B 3/0091* (2013.01); *A61B 3/102* (2013.01); *A61B 3/1005* (2013.01); *A61B 3/107* (2013.01); *A61B 3/1225* (2013.01); *A61B 3/14* (2013.01); *A61B 3/18* (2013.01); *A61B 8/10* (2013.01); *A61B 3/10* (2013.01); *A61B 5/7275* (2013.01)

(58) Field of Classification Search
CPC ......... A61B 3/107; A61B 3/1225; A61B 3/14; A61B 3/18; A61B 3/10; A61B 3/145; A61B 5/7275; A61B 8/10
USPC ....... 351/200, 205, 206, 208, 210–212, 214, 351/221, 246; 600/427, 437
See application file for complete search history.

(56) References Cited

U.S. PATENT DOCUMENTS

| | | |
|---|---|---|
| 2003/0142271 A1 | 7/2003 | Ross et al. |
| 2006/0209256 A1 | 9/2006 | Beyerlein et al. |
| 2009/0161068 A1 | 6/2009 | Lai et al. |
| 2012/0197102 A1 | 8/2012 | Hanebuchi et al. |
| 2013/0100408 A1 | 4/2013 | Simpson |
| 2017/0360294 A1* | 12/2017 | Satake ................. A61B 3/1225 |
| 2018/0074344 A1* | 3/2018 | Kobayashi ........... A61B 3/0025 |
| 2020/0100673 A1* | 4/2020 | Shimizu .................. A61B 3/14 |
| 2020/0221947 A1* | 7/2020 | Mino .................. A61B 3/0025 |

FOREIGN PATENT DOCUMENTS

| | | |
|---|---|---|
| EP | 2653095 A1 | 10/2013 |
| EP | 3210526 A1 | 8/2017 |
| EP | 3222204 A1 | 9/2017 |
| JP | H0531073 A | 2/1993 |
| WO | 2014074157 A1 | 5/2014 |

* cited by examiner

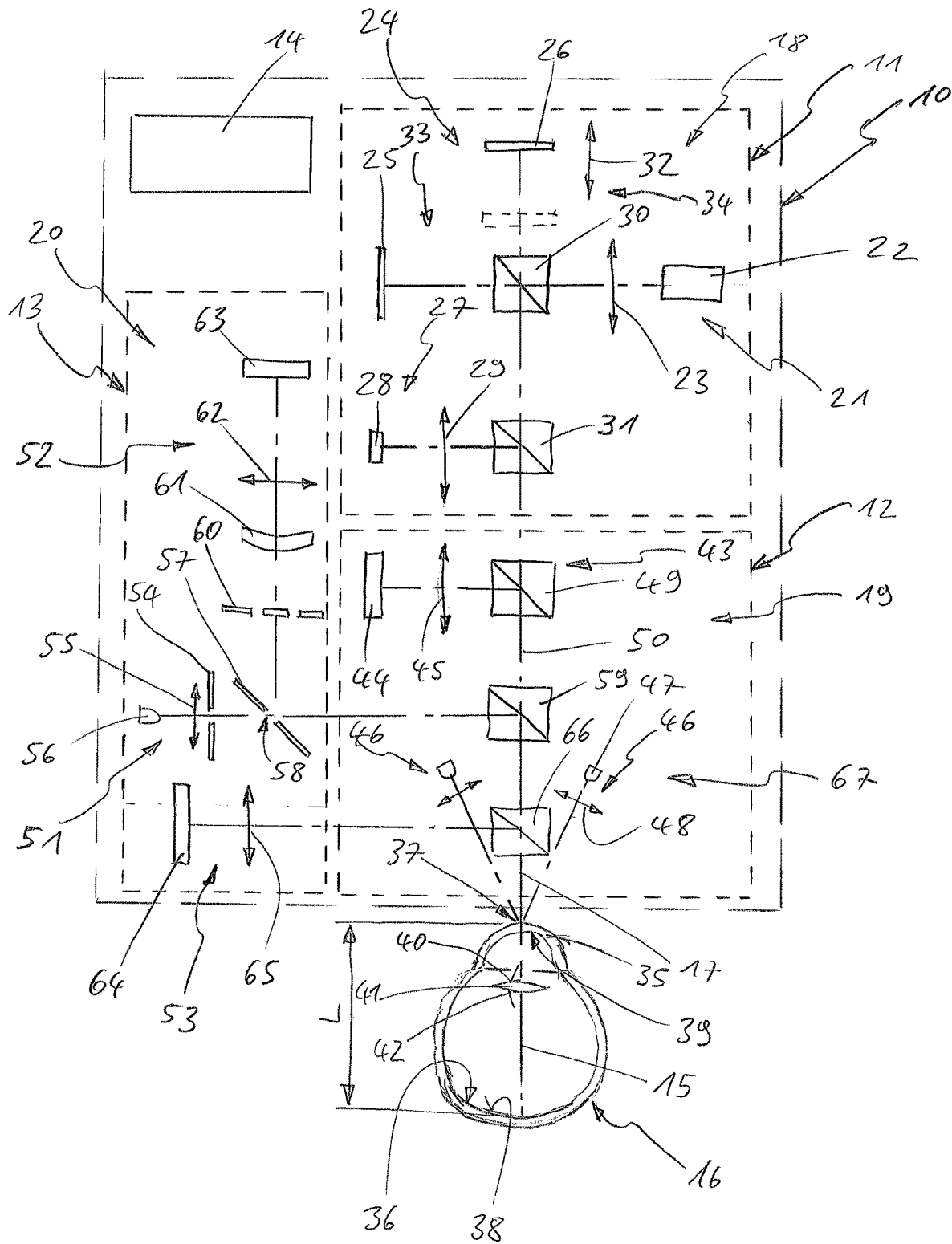

METHOD AND VISION TESTING SYSTEM FOR TESTING THE EYES

CROSS-REFERENCE TO RELATED APPLICATIONS

This application claims priority to German Patent Application No. 10 2019 101 409.3 filed Jan. 21, 2019. The contents of this application are hereby incorporated by reference as if set forth in its entirety herein.

The disclosure relates to a method for testing the eyes of a test person and to a vision testing system.

Refractive measuring devices are sufficiently known and routinely serve for determining a refraction value of an eye of a test person. The refraction value can be utilized for evaluating an optical ametropia of the eye. A frequent form of ametropia is myopia where a focal plane is in front of the retina, which results in a blurred visual impression. A distinction is made between different forms of myopia. With the so-called axial myopia, an axial length of the eye is increased. With refraction myopia, the refractive power of the refractive parts of the eye, for example the cornea or the lens, is increased. The increased refractive power can, for example, be caused by an increased curvature of a refractive surface such as the cornea. A refractive index of the lens is changed so that an increased refractive power arises. Myopia can already be developed in childhood due to different environmental factors such as visual tasks in the close range of the eye or with advancing age, for example due to a decrease in the accommodation capability of the ciliary muscle with the lens. Apart from a medication intake, diseases such as diabetes mellitus or a genetic disposition may also be the reason for myopia.

With the aid of a refractive measuring device, a refraction value can comparatively easily be determined objectively in diopters (dot). For instance, a vision testing system is known from DE 102 006 017 389 A1 that is formed from a refractive measuring device and from a topographic measuring device. The refractive measuring device is in this case an autorefractometer that is combined with the topographic measuring device that is realized in the manner of a keratometer. With the aid of the keratometer, a topography of the cornea can be determined, which makes it possible to gain information on a possible cause of myopia, for example a supposed cataract.

Nevertheless, evaluating the refraction and topography data that have been obtained in this way is difficult since the refraction measurement may be faulty and other influencing factors may also be the cause of certain refraction values. A faulty refraction measurement may, for example, arise when the test person, during the measurement, accommodates in the close range with the eye. In order to rule this out, the ciliary muscle can be paralyzed by medication (cycloplegia), which is, however, time-consuming and unpleasant for the test person.

The present disclosure is therefore based on the object of proposing a method and a vision testing system with the aid of which a refraction value can be determined easily and reliably.

The disclosed method for testing the eyes of a test person is carried out with the aid of a vision testing system that comprises a first measuring device, a second topographic measuring device, a third refractive measuring device and a processing means, an axial length of an eye of the test person being measured with the aid of the first measuring device, a curvature of the cornea of the eye being measured with the aid of the second measuring device, a refractive property of the eye being measured with the aid of the third measuring device, a measurement simultaneously being carried out with the first, second and third measuring device at the eye, measurement data of the measurements of the first, second and third measuring device being processed with the aid of the processing means, said processing means presenting a database with normal data, a comparison of the measurement data with the normal data being carried out and a result of said comparison being issued by means of said processing means.

Due to the fact that the axial length of the eye, the curvature of the cornea of the eye and the objective refractive property or a refraction value of the eye in, for example, diopters are measured at the same time, measurement errors, as they may occur in successive measurements with the aid of different measuring instruments, can be precluded. When the first, second and third measuring device perform measurements at the same time, all measurement data obtained refer to a state of the eye at this point in time, which makes it possible to compare the measurement data under the same conditions. When using different apparatuses or when measurements are performed one after another, the eye is always oriented differently with respect to a measurement axis as a consequence of eye movements or is in different accommodation states. Apart from determining the refraction value objectively, measurement data for the topography or the curvature of the cornea as well as the axial length of the eye can be identified with the method. Owing to these measurement data, which are then available at the same time, a person carrying out the examination can more easily evaluate the measured refraction value.

In particular due to the fact that the processing means comprises the database with the normal data and carries out the comparison of the measurement data with the normal data, a deviation can easily be evaluated on the basis of the result of the comparison or the respective difference between a measurement value and a normal value. If, for example, a measurement value for the curvature of the cornea deviates from a normal value to a large extent, the person carrying out the examination can more easily interpret a refraction value that also deviates from the normal value. In the example that has been mentioned before, the curvature of the cornea may be the cause of the refraction value. Furthermore, a person carrying out the examination can determine an axial length that is too large to be the reason for a refraction value. If there are no measurement values of the curvature of the cornea and of the axial length of the eye that deviate from a normal value, a refraction index of the lens may, for example, be different. All in all, it becomes possible, due to the fact that the measurement values are obtained simultaneously, to obtain precise measurement values easily and quickly and to compare them with normal values. Here, the processing means performs the comparison and issues a result of the comparison, making it in this way possible for a person carrying out the examination to evaluate the obtained measurement data more easily. Here, the processing means comprises means for data processing and display such as a computer and a screen.

By means of the processing means, a degree of the refraction is determined by way of the comparison of the measurement data with the normal data. With the aid of the degree of the refraction, the identified measurement values can be categorized in relation to the normal data that are included in the database on the basis of the deviation from the normal data. The processing means can identify a degree of an objective refraction on the basis of the physical quantities of the measurement values. Here, the measurement values can be weighted differently or the measurement values can be put into relation to one another. The processing means can issue the degree of the objective refraction, for example on a screen so that it becomes possible to evaluate the refractive properties of the eye even more easily.

As normal data, measurement data of eyes of a normal population, with an axial length of an eye, a curvature of the cornea of the eye and a refractive property of the eye, may be used. The normal data can correspond to the fiftieth percentile of a comparison group of persons at whose eyes the measurement data were identified. The normal data may also include all measurement data of the comparison group, the processing means then being able to issue a precise deviation of the measurement data that has been identified with the aid of the vision testing system from the fiftieth percentile of the comparison group, for example also an indication on to which percentile of the comparison group the measurement data can in each instance be assigned. A representative population average is understood to be the comparison group that is referred to as normal population here.

Advantageously, the processing means can in each instance compare the measured axial length, the curvature and the refractive property of the eye with the normal data of the axial length, the curvature and the refractive property of an eye, said processing means being configured to select the normal data for the comparison according to a consistency of the axial length, the curvature or the refractive property with the measurement data of the measurement. The processing means can accordingly not only compare the respective records of measurement data and normal data for the axial length, the curvature and the refractive property independently, but it can also select, from the database or the normal data, an eye or the normal data associated with said eye or the measurement data that come closest to the measurement data that have been measured with the aid of the vision testing system or correspond to them. The processing means accordingly compares the eye measured with the aid of the vision testing system and the eyes that are included in the database in the form of measurement data and issues this comparison. A person carrying out the examination can, on the basis of the comparison, even more easily evaluate to what extent the eye measured with the aid of the vision testing system deviates from a standard or already shows known symptoms.

The processing means can take an age of the test person into account when comparing the measurement data. The database having the normal data can likewise include normal data that can in each instance be assigned to an indication of the age. The processing means, for the comparison, can then select the normal data that correspond to the age of the test person from the database having the normal data. The age of the test person can, for example, be entered into the processing means via input means before or after a measurement. Owing to the known connection between myopia and the age, an even more precise comparison of the measurement data becomes possible by taking into account the age. In addition, it is possible that the processing means, when comparing the measurement data, for example takes a prevalence of myopia in the population into account. Apart from age, job profiles and dispositions can then also be taken into account.

Measurement data of the test person that were determined at a point of time before the measurement, with an axial length of the eye, a curvature of the cornea of the eye and a refractive property of the eye, can be used as normal data. In this way, it is possible to take measurements of the same test person, with the aid of the vision testing system, at different points of time and to obtain and store measurement data in each instance. These measurement data can then be used as normal data for the comparison. In this way, a potential change in the optical property of the relevant eye can be determined over a period of, for example, months or years. A cause of a refraction value that deteriorates, for example, can in this way be identified even more easily. Optionally, it is, however, also possible to always compare the measurement data measured at each measuring time with normal data of a comparison group.

The processing means is able to correct the measurement data of the third measuring device with the aid of the measurement data of the first measuring device and/or of the second measuring device. Determining an objective refraction value is often difficult and prone to errors since the refraction may be influenced by many factors and environmental conditions, as pointed out above. The curvature of the cornea and the axial length, however, are measurement values that are not subject to, for example, the influence of medicine or brain activity. The measurement data of the third measuring device can therefore advantageously be corrected with the aid of the measurement data of the first and/or second measuring device.

In this way, the processing means is configured to carry out a plausibility check for a measured objective refraction value of the eye with the axial length and/or with the curvature of the cornea of the eye and to correct, when the refraction value differs, said refraction value according to the axial length and/or the curvature of the cornea. Here, the plausibility check can be performed on the basis of range indications that state a tolerance range for the respective measurement values. The range indications may also be stored in the database. The range indications may be based on experience or may be determined on the basis of a standard deviation with the aid of statistical averages.

A fixation mark that can be focused by the eye at infinity can be displayed by means of a fixation means of the vision testing system, the eye being able to focus on the fixation mark and the eye being able to be fixed in relation to the vision testing system. A correct position of the eye in relation to a measurement axis of the vision testing system is essential for a precise measurement of the vision testing system. Advantageously, an optical axis of the eye is aligned with the measurement axis of the vision testing system here. Here, the eye can be positioned in that the fixation mark is presented to the test person, the test person being able to focus on said fixation mark at infinity. The fixation mark may, for example, be an image representation of an object. A screen that is coupled into an optical path of the vision testing system may perform the image representation. It is essential that the image representation for the eye of the test person is at infinity so that the ciliary muscle of the eye is completely relaxed during the measurement with the aid of the vision testing system.

Advantageously, the eyes can then also be tested without administering cycloplegic agents. It is thus possible to test the eyes more easily and faster.

The vision testing system in accordance with the disclosure for testing the eyes of a test person comprises a first interferometric measuring device, a second topographic measuring device, a third refractive measuring device and a processing means, an axial length of an eye of the test person being measurable with the aid of the first measuring device, a curvature of the cornea of the eye being measurable with the aid of the second measuring device, a refractive property of the eye being measurable with the aid of the third measuring device, the first, second and third measuring device being configured to simultaneously carry out a measurement at the eye, said processing means being configured to process measurement data of the measurements of the first, second and third measuring device, said processing means presenting a database with normal data, said processing means being configured to carry out a comparison of the measurement data with the normal data and to issue a result of said comparison. With regard to the advantages of the vision testing system in accordance with the disclosure, reference is made to the description of the advantages of the method in accordance with the disclosure.

The first measuring device, the second measuring device and the third measuring device may present a common measurement axis that can be harmonizable with an optical axis of the eye. Due to the fact that the measuring devices present a common measurement axis, it becomes possible to obtain measurement data in a particularly precise and easily comparable fashion. It is in particular advantageous for precisely determining an axial length of the eye if the common measurement axis is aligned with the optical axis of the eye.

The second measuring device and/or the third measuring device may present a distance measurement means for measuring a distance between the eye and the second measuring device and/or third measuring device. The distance measurement means can measure the distance between the refractive measuring device and/or the topographic measuring device and the eye to be examined. This distance is essential for a correction of the measurement data and it becomes possible, by obtaining distance data, to position the test person correspondingly correctly in front of the vision testing system or to suitably correct the measurement data that have been measured with the aid of the refractive measuring device. In this way, the distance between the refractive measuring device and the cornea of the eye, in particular the front face of the cornea, may advantageously be measurable with the aid of the distance measurement means. In addition, a distance from the retina or rear face of the eye can also be determined with the aid of the distance measurement means, taking into account the axial length. Optionally, a distance from a rear face of the cornea, a front face of the lens and/or a rear face of the lens can also be determined. The type of construction of the distance measurement means is in principle arbitrary, said distance measurement means being realizable by the topographic measuring device, by a keratometer or by a Scheimpflug system.

The first measuring device, the second measuring device and/or the third measuring device may present a fixation means for fixing the eye in relation to the vision testing system. The fixation means may, for example, comprise a screen or a suitable projector, with the aid of which a fixation mark for the eye can be visibly represented at infinity. The fixation mark may be an image representation of an object so that a focusing of the eye onto one point is avoided. The fixation mark may be coupled into an optical path of the vision testing system via, for example, a splitter cube so that the fixation mark is visible for the test person.

The first measuring device may be a partial coherence interferometer (PCI), said interferometer being designed to have a coherent light source, two measuring arms and a detector means for simultaneously capturing the front face of the cornea and the retina or an optical boundary surface of the eye. Due to the fact that the interferometer disposes of two measuring arms, it is possible to detect the front face of the eye and the retina at the same time and to determine a relative distance of the front face and the retina and consequently the axial length of the eye. Here, it is unimportant which distance the eye has in relation to the vision testing system since the distance or the axial length of the eye can be measured independently of the distance from the vision testing system with the aid of the interferometer. Any measuring errors of the interferometer owing to a spaced position of the eye in relation to the vision testing system can in this way be entirely eliminated. The axial length can consequently particularly precisely be measured. Apart from the axial length, other optical boundary surfaces of the eye such as the rear face of the cornea, the front face of the lens, the rear face of the lens and distances between the optical boundary surfaces can be measured with the aid of the interferometer and can be processed by the processing means. These measurement data can also be utilized by the processing means for a comparison with corresponding normal data.

The second measuring device may be a keratometer and/or a Scheimpflug system. With the aid of such measuring devices, it is possible to determine a topography or the curvature of the cornea of the eye.

The keratometer may present an examination means having a camera and measuring marks that can be captured with the aid of the camera and that can be realized by a fluorescent strip that is circular and not collimated and by two collimated luminous spots. A type of construction of the measuring marks of the keratometer is basically arbitrary, light emitting diodes being envisagable as an illuminant. The fluorescent strip may be generated by a circular light conductor element. It may also be envisaged to generate a plurality of concentric annular fluorescent strips. Advantageously, as the light for the measuring marks, infrared light may be used. The examination means may be a camera that is coupled into an optical path of the vision testing system or of the keratometer via a splitter cube. With the aid of the camera, a parasitic image of the measuring marks on the cornea of the eye can be captured. By means of image processing, a curvature of the cornea can easily be derived from the parasitic image of the measuring marks and can be displayed by the processing means. Furthermore, it is possible to use the camera as a setup camera or as an overview camera for the vision testing system for the precise arrangement and orientation of the eye of the test person.

The Scheimpflug system may present a projection means that may be designed for illuminating the eye with a light gap and an examination means having a camera that may be designed for capturing a sectional view of the light gap in the eye, said projection means and the camera being configured to be disposed in relation to each other according to the Scheimpflug principle. With the aid of the projection means, the light gap can then be projected onto the eye so that a gap illumination of the eye along the optical axis of the eye or of the visual axis can be performed. With the aid of the camera that is disposed according to the Scheimpflug principle, the sectional view of the light gap in the eye that is generated in this way can be captured so that an illuminated cross-sectional area of the eye or a front portion of the eye can optically be capturable. A longitudinal sectional view of the eye that results in this way can then advantageously reproduce the optical boundary surfaces of the cornea and of the lens. The processing means can easily calculate the relative distances of the optical boundary surfaces from a set of image data that has been obtained in this way. Furthermore, the curvature of the cornea can also easily be identified. The Scheimpflug system may realize the second measuring device alone or also together with the keratometer.

Advantageously, the third measuring device may be an auto refractometer.

The autorefractometer may present a projection means that may be designed for projecting a lighting pattern onto the retina of the eye and an examination means, having a diffraction unit and a camera that may be designed for capturing the lighting pattern in the eye. Here, the lighting pattern may be projected in such a way that the lighting pattern is focused on the retina. With the aid of the optical examination means, the lighting pattern that is reflected at the retina can be examined through the lens of the eye so that an image pattern is displayed on a photoelectric sensor of the camera. This image pattern is captured by the camera and is evaluated by means of image editing. Corresponding to the refractive properties of the eye, the lighting pattern that is projected onto the retina is characteristically distorted so that the refractive properties of the eye can be derived within the framework of analyzing the lighting pattern from a degree of distortion. The diffraction unit may, for example, be an aperture plate having a number of holes that are disposed in a circle, the optical paths of the holes in each instance being deflectable onto the sensor of the camera via a deflection prism or a corresponding lens. Alternatively, the diffraction unit may also be a diffractive optical element (DOE).

Other advantageous embodiments of a vision testing system result from the description of the features contained in the dependent claims that relate back to method claim 1.

In the following, the disclosure is explained in more detail with reference to the enclosed drawing.

The FIGURE shows a schematic illustration of a construction of a vision testing system 10 comprising a first interferometric measuring device 11, a second topographic measuring device 12, a third refractive measuring device 13 and a processing means 14. The vision testing system 10 is disposed in relation to a visual axis 15 or optical axis of an eye 16 to be examined in such a way that the visual axis 15 corresponds to a measurement axis 17 of the vision testing system 10. The first interferometric measuring device 11 is realized by a partial coherence interferometer 18, the second topographic measuring device 12 is realized by a keratometer 19 and the third refractive measuring device 13 is realized by an autorefractometer 20.

The interferometer 18 is essentially realized by a laser means 21 having a laser light source 22 and a lens arrangement 23, a mirror means 24 having a first mirror 25 and a second mirror 26, a detector means 27 having a detector 28 and a lens arrangement 29 as well as a first splitter cube 30 and a second splitter cube 31. In particular the second mirror 26 displaced so as to be longitudinally displaceable along the double arrow 32 so that a length of a second reference arm 34 or of a corresponding reference path can be changed. A first reference arm 33 is, however, not realized in such a way that its length can be changed. Through a displacement of the second mirror 26, different regions of the eye 16 that are located on the visual axis 15 can be scanned. In particular, it is possible to measure an axial length (L) of the eye 16 from the cornea 35 up to the retina 36 or from a front face 37 of the cornea 35 up to a rear face 38 of the retina 36. A more profound explanation of a known function of the partial coherence interferometer 18 is omitted here. Furthermore, measurement data may also be obtained that describe relative positions of optical boundary surfaces on the visual axis 15, such as the front face 37 of the cornea 35, the rear face 39 of the cornea 35, a front face 40 of a lens 41, a rear face 42 o the lens 41 and the rear face 38 of the retina 36.

The keratometer 19 comprises an examination means 43 having a camera 44 and a lens arrangement 45 as well as measuring marks 46 that can be captured with the aid of the camera 44 and that are in each instance realized by an infrared light source 47 and by a lens arrangement 48. The infrared light source may, for example, be a light emitting diode. The measuring marks 46 may realize two collimated luminous spots on the cornea 35 that can be captured with the aid of the camera 44. The measuring marks 46 are supplemented by a fluorescent strip that is circular and not collimated and that is not illustrated. The examination means 43 is coupled into an optical path 50 of the vision testing system 10 via a splitter cube 49.

The autorefractometer 20 serves to determine the refractive properties of the eye 16 and essentially comprises a projection means 51 and an examination means 52 as well as a fixation means 53. With the aid of the optical projection means 51, a lighting pattern can be projected onto the retina 36 of the eye 16 and be focused there. Here, the projection means 51 comprises an aperture plate 54, a lens arrangement 55 and an infrared light source 56. The lighting pattern is coupled into the optical path 50 of the vision testing system through a mirror 57 having an aperture plate 58 via a first splitter cube 59 of the autorefractometer 20. The optical examination means 52 comprises a 6-fold aperture plate 60, a deflection prism 61, a lens arrangement 62 and a camera 63. The image data that are captured with the aid of the camera 63 are processed and evaluated in the processing means 14 in order to determine the refractive properties of the eye 16. The examination means 52 is coupled into the optical path 50 via the mirror 57 and the first splitter cube 59.

The fixation means 53 of the autorefractometer 20 is realized by a screen 64 for the image representation of a fixation mark and by a lens arrangement 65 for displaying the fixation mark at infinity. A second splitter cube 66 makes it possible to couple the fixation mark into the optical path 50. The first splitter cube 59 and the second splitter cube 66 are parts of the autorefractometer 20.

Furthermore, a distance measurement means 67 is envisaged that is realized by the keratometer 19 here. The distance measurement means 67 comprises the measuring marks 46 and the examination means 43.

With the vision testing system 10 that is illustrated here, a measurement is performed at the same time with the first measuring device 11, the second measuring device 12 and the third measuring device 13, the processing means 14 processing measurement data of the measurement of the first measuring device 11, the second measuring device 12 and the third measuring device 13, said processing means 14 presenting a database that is not illustrated here, having normal data, a comparison of the measurement data with the normal data being carried out and a result of said comparison being issued by means of said processing means 14.

The invention claimed is:

1. A method for testing the eyes of a test person with the aid of a vision testing system, comprising a first measuring device, a second topographic measuring device, a third refractive measuring device and a processing means, an axial length (L) of an eye of the test person being measured with the aid of the first measuring device, a curvature of the cornea of the eye being measured with the aid of the second measuring device, a refractive property of the eye being measured with the aid of the third measuring device, a measurement simultaneously being carried out with the first, second and third measuring device at the eye, measurement data of the measurements of the first, second and third measuring device being processed with the aid of the processing means, said processing means presenting a database with normal data including measurement data of a normal population that are taken by the vision testing system, a comparison being carried out of the measurement data with the normal data associated with the measurement data that come closest to the measurement data that have been measured with the aid of the of the vision testing system and a result of said comparison being issued by means of said processing means.

2. The method according to claim 1, wherein a degree of the refraction is determined by means of the processing means by way of the comparison of the measurement data with the normal data.

3. The method according to claim 1, wherein as normal data, measurement data of eyes of a normal population, with an axial length (L) of an eye, a curvature of the cornea of the eye and a refractive property of the eye, are used.

4. The method according to claim 3, wherein the processing means in each instance compares the measured axial length (L), the curvature and the refractive property of the eye with the normal data of the axial length (L), the curvature and the refractive property of an eye, said processing means selecting the normal data for the comparison according to a consistency of the axial length (L), the curvature or the refractive property with the measurement data of the measurement.

5. The method according to claim 1, wherein the processing means takes an age of the test person into account when comparing the measurement data.

6. The method according to claim 1, wherein measurement data of the test person that were determined at a point of time before the measurement, with an axial length (L) of the eye, a curvature of the cornea of the eye and a refractive property of the eye, are used as normal data.

7. The method according to claim 1, wherein the processing means corrects the measurement data of the third measuring device with the aid of the measurement data of the first measuring device and/or of the second measuring device.

8. The method according to claim 7, wherein the processing means carries out a plausibility check for a measured objective refraction value of the eye with the axial length (L) and/or with the curvature of the cornea of the eye and corrects, when the refraction value differs, said refraction value according to the axial length (L) and/or the curvature of the cornea.

9. The method according to claim 1, wherein a fixation mark that can be focused by the eye at infinity is displayed by means of a fixation means of the vision testing system, the eye focusing on the fixation mark and the eye being fixed in relation to the vision testing system.

10. The method according to claim 1, wherein the eyes are tested without administering cycloplegic agents.

11. A vision testing system for testing the eyes of a test person with the aid of a vision testing system, comprising a first measuring device, a second topographic measuring device, a third refractive measuring device and a processing means, an axial length (L) of an eye of the test person being measured with the aid of the first measuring device, a curvature of the cornea of the eye being measured with the aid of the second measuring device, a refractive property of the eye being measured with the aid of the third measuring device, the first, second and third measuring device being configured to simultaneously carry out a measurement at the eye, said processing means being configured to process measurement data of the measurements of the first, second and third measuring device, said first, second and third measuring device being integrated in one piece of equipment, wherein said processing means presents a database with normal data including measurement data of eyes of a normal population that are taken by the vision testing system, with an axial length (L) of an eye, a curvature of the cornea of the eye, and a refractive property of the eye, and wherein the processing means in each instance compares the axial length (L), the curvature, and the refractive property of the eye as measured with the normal data of the axial length (L), the curvature, and the refractive property of an eye from the database, said processing means selecting the normal data associated with the measurement data that come closest to the measurement data that have been measured with the aid of the of the vision testing system for the comparison according to a consistency of the axial length (L), the curvature, or the refractive property with the measurement data of the measurement.

12. The vision testing system according to claim 11 said processing means being configured to carry out a comparison of the measurement data with the normal data and to issue a result of said comparison.

13. The vision testing system according to claim 11, wherein the first measuring device, the second measuring device and the third measuring device present a common measurement axis that can be harmonized with the optical axis of the eye.

14. The vision testing system according to claim 11, wherein the second measuring device and/or the third measuring device present or presents a distance measurement means for measuring a distance between the eye and the second measuring device and/or third measuring device.

15. The vision testing system according to claim 11, wherein the first measuring device, the second measuring device and/or the third measuring device present/s a fixation means for fixing the eye in relation to the vision testing system.

16. The vision testing system according to claim 11, wherein the first measuring device is an ultrasonic measuring device.

17. The vision testing system according to claim 11, wherein the first measuring device is an interferometric measuring device.

18. The vision testing system according to claim 17, wherein the first measuring device is an interferometer for optical coherence interferometry (OCT).

19. The vision testing system according to claim 17, wherein the first measuring device is a partial coherence interferometer, said interferometer being designed to have a coherent light source, two measuring arms and a detector means for simultaneously capturing the front face and the retina of the eye.

20. The vision testing system according to claim 11, wherein the second measuring device is a keratometer and/or a Scheimpflug system.

21. The vision testing system according to claim 20, wherein the keratometer presents an examination means having a camera and measuring marks that can be captured with the aid of the camera and that are realized by a fluorescent strip that is circular and not collimated and by two collimated luminous spots.

22. The vision testing system according to claim 20, wherein the Scheimpflug system presents a projection means that is designed for illuminating the eye with a light gap and an examination means having a camera that is designed for capturing a sectional view of the light gap in the eye, said projection means and the camera being disposed in relation to each other according to the Scheimpflug principle.

23. The vision testing system according to claim 11, wherein the third measuring device is an autorefractometer.

24. The vision testing system according to claim 23, wherein the autorefractometer presents a projection means that is designed for projecting a lighting pattern onto the retina of the eye and an examination means, having a diffraction unit and a camera that is designed for capturing the lighting pattern in the eye.

* * * * *